US009381154B2

(12) United States Patent
Zhou et al.

(10) Patent No.: US 9,381,154 B2
(45) Date of Patent: Jul. 5, 2016

(54) DIRECT INKJET FABRICATION OF DRUG DELIVERY DEVICES

(75) Inventors: Jing Zhou, Webster, NY (US); Shu Chang, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 473 days.

(21) Appl. No.: 13/156,503

(22) Filed: Jun. 9, 2011

(65) Prior Publication Data

US 2012/0315333 A1  Dec. 13, 2012

(51) Int. Cl.
| | |
|---|---|
| *A61K 9/20* | (2006.01) |
| *C09D 11/34* | (2014.01) |
| *A61K 9/00* | (2006.01) |
| *A61K 9/24* | (2006.01) |

(52) U.S. Cl.
CPC .............. *A61K 9/0056* (2013.01); *A61K 9/209* (2013.01); *A61K 9/2095* (2013.01)

(58) Field of Classification Search
CPC .............................. A61K 9/2095; C09D 11/34
See application file for complete search history.

(56) References Cited

U.S. PATENT DOCUMENTS

| | | | | |
|---|---|---|---|---|
| 4,390,369 | A | * | 6/1983 | Merritt .................... C09D 11/34 106/31.3 |
| 4,548,825 | A | | 10/1985 | Voss et al. |
| 5,387,380 | A | * | 2/1995 | Cima et al. ....................... 264/69 |
| 5,490,962 | A | * | 2/1996 | Cima et al. ..................... 264/401 |
| 5,669,965 | A | * | 9/1997 | Sawada ................... C09D 11/34 106/31.29 |
| 5,788,751 | A | * | 8/1998 | Sawada ................... C09D 11/34 106/31.29 |
| 5,800,600 | A | * | 9/1998 | Lima-Marques ....... C09D 11/34 106/31.29 |
| 5,800,601 | A | * | 9/1998 | Zou et al. .................... 106/31.65 |
| 6,113,678 | A | * | 9/2000 | Malhotra ................ C09D 11/34 106/31.29 |
| 6,280,771 | B1 | * | 8/2001 | Monkhouse et al. ......... 424/484 |
| 2003/0101902 | A1 | * | 6/2003 | Reitnauer ............. A01J 27/005 106/31.31 |
| 2003/0143268 | A1 | | 7/2003 | Pryce Lewis et al. |
| 2004/0005360 | A1 | * | 1/2004 | Wang et al. .................... 424/473 |
| 2007/0231435 | A1 | * | 10/2007 | Ream et al. .................... 426/383 |
| 2007/0259010 | A1 | * | 11/2007 | Yoo et al. ....................... 424/400 |
| 2008/0026040 | A1 | * | 1/2008 | Farr et al. ....................... 424/443 |
| 2010/0166934 | A1 | * | 7/2010 | Caiger ..................... A23L 1/275 426/572 |
| 2012/0035081 | A1 | * | 2/2012 | Lin .................... B01L 3/502707 506/13 |

FOREIGN PATENT DOCUMENTS

WO          0029202          5/2000

OTHER PUBLICATIONS

Lam et al. ("Comparison of the degradation of polycaprolactone and polycaprolactone-(b-tricalcium phosphate) scaffolds in alkaline medium", Polymer International, 2007, 56, 718-728).*
Masood ("Application of fused deposition modelling in controlled drug delivery devices", Assembly Automation, 2007, 27(3), 215-221.*
Ramsay et al. ("Methylene blue and serotonin toxicity: inhibition of monoamine oxidase A (MAO A) confirms a theoretical prediction" British Journal of Pharmacology, 2007, 152, 946-951).*
Pekarovicova et al. ("Phase-Change Inks", Journal of Coatings Technology, 2003, 75(936), 65-72).*
Chovancova, Veronika, Alexandra Pekarovicova, and Paul D. Fleming. "Hot Melt Inks for 3D Printing." NIP & Digital Fabrication Conference. vol. 2005. No. 3. Society for Imaging Science and Technology, 2005.*
Sastry, Srikonda Venkateswara, Janaki Ram Nyshadham, and Joseph A. Fix. "Recent technological advances in oral drug delivery—a review." Pharmaceutical science & technology today 3.4 (2000): 138-145.*
Yu, Deng Guang et al. Three-dimensional printing in pharmaceutics: promises and problems. Journal of Pharmaceutical Sciences. Sep. 2008, 97(9):3666.
'Printing' Pills to Order: Research to Create safer, Faster-Acting Medicines. ScienceDaily. May 24, 2010:1-2. http://www.sciencedaily.com/releases/2010/05/100524073001.htm.
European Search Report from European Patent Application No. 12 17 0415.9 dated Sep. 26, 2012, 10 Pages.
Katstra, We et al., Oral dosage forms fabricated by Three Dimensional Printing™, Journal of Controlled Release, May 1, 2000, vol. 66, No. 1, pp. 1-9.
Rowe, C.W. et al. Multimechanism oral dosage forms fabricated by three dimensional printing™, Journal of Controlled Release, May 1, 2000, vol. 66, No. 1, pp. 11-17.

* cited by examiner

*Primary Examiner* — Bethany Barham
*Assistant Examiner* — Peter Anthopolos
(74) *Attorney, Agent, or Firm* — MH2 Technology Law Group LLP

(57) ABSTRACT

In some aspects of the present application, a method of forming one or more layers of at least a portion of a drug delivery device (DDD) is described. The method can include providing a substrate; providing one or more DDD components that are dissolved or dispersed in one or more pharmaceutically compatible phase change inks; ejecting, by one or more nozzles, a first portion of the one or more pharmaceutically compatible phase change inks to form a first layer on the substrate; and ejecting, by the one or more nozzles, a second portion of the pharmaceutically compatible phase change inks to form a second layer over the first layer.

16 Claims, 2 Drawing Sheets

DIRECT INKJET FABRICATION OF DRUG DELIVERY DEVICES

DESCRIPTION OF THE DISCLOSURE

1. Field of the Disclosure

The present application is directed to a drug delivery devices, and more particularly to a method and system for direct inject fabrication of drug delivery devices.

2. Background of the Disclosure

About two third of all prescriptions are in solid dosage forms, and half of these are compressed tablets. Tablets are produced pretty much the same way in pounds or in tons, depending on their medical purposes and newness. There is also a demand for better methodology to achieve more rapid prototyping and time-to-market. The conventional tablets manufacture method is also very limited for creating novel drug delivery devices (DDD) that requires excellent control of microstructure and spatial distribution of API or exicipents inside tablet. Although three-dimensional printing (3DP) provides an alternative approach of manufacturing novel tablet based DDD, the need of powder bed, possible cross contamination, poor mechanical strength, low drug loading are problems of this technology.

Currently, there are several issues with 3DP manufactured tablets. 3DP requires a powder bed that can lay out a thin and uniform layer of powders. Fine powders are preferable because it gives better binder effect, smoother surfaces, smaller feature size, thinner layer that will eliminate slicing defects such as stair-stepping. However, fine powders are difficult to spread into smooth layers due to their affinity to agglomerate, adhere to walls and poor flowability. These materials property challenges will lead to uneven densification within layers and consequently in the final tablets. Further, drop-impact ballistic ejection and erosion are also problems when using fine powders.

Binder liquids tend to migrate through the powders, which is referred to as bleeding. Excessive binder bleeding creates rough surfaces, failure of the intended drug release due to poor spatial resolution.

After each manufacture cycle, tablets are removed from powder bed and leave a large portion of unused powders. To minimize the waste, recycling the unused powders can cause potential cross contamination. Cross contamination will become worse when different powders are used in the fabrication because of the difficulties in cleaning fine particles.

Powders are not essentially required for making tablets for many medications. Powder based solid dosage form has advantage for rapid drug release because of its fast disintegration and dissolution, but are not always the best choice for other controlled drug releases, such as sustained drug release.

The mechanical strength of tablets is used as a quality controlling parameter to ensure that tablets can withstand subsequent handling procedures. Unlike conventional compressed tablets, tablets made by 3DP have poor mechanical performance because they are simply loose powders bound by liquid binder.

Although 3DP is effective for high potent, whose low dosages are needed for therapeutic effects, a large majority of new chemical entities and many existing drug molecules are poorly soluble or lipophilic. High dosages are often needed in 3DP fabrication to achieve the desired therapeutic effects. Limited void spaces in the layered powder, poor solubility of the drugs, and the dimensions of DDD are the disadvantages of 3DP in the fabrication of DDD with sufficient drug loading.

Moreover, the conventional uses of 3DP with aqueous and solvent-based inks require extra powders as supporting materials for the DDD. Further, the aqueous and solvent-based inks require other means to dry the water or solvent and less than 5% of the jetted materials are used in the final DDD.

SUMMARY OF THE DISCLOSURE

In accordance with some aspects of the present disclosure, a method is disclosed. The method can include forming one or more layers of at least a portion of a drug delivery device (DDD) by ejecting one or more DDD components through one or more nozzles of a three-dimensional printing (3DP) system, wherein the one or more DDD components are dissolved or dispersed in one or more pharmaceutically compatible phase change inks.

In accordance with some aspects of the present disclosure, a method of forming one or more layers of at least a portion of a drug delivery device (DDD) is described. The method can include providing a substrate; providing one or more DDD components that are dissolved or dispersed in one or more pharmaceutically compatible phase change inks; ejecting, by one or more nozzles, a first portion of the one or more pharmaceutically compatible phase change inks to form a first layer on the substrate; and ejecting, by the one or more nozzles, a second portion of the pharmaceutically compatible phase change inks to form a second layer over the first layer.

In some aspects, the 3DP system can include one or more nozzles that are equipped to be controlled by one or more controllers. The one or more nozzles can dispense the DDD components stored in one or more DDD component reservoirs. The one or more DD components can include one or more active pharmaceutical ingredients (API), one or more excipients, or both one or more API and one or more excipients. Reservoirs can also include other components, for example, but not limited to, coloring agents, dyes or pigments that be dispensed by the nozzles. These other components can also be added directly to the phase change inks to be dispensed by the nozzles.

In some aspects, the phase change inks can have a phase change temperature between, for example, but not limited to, 40 and 200° C., or more particularly a phase change temperature between 60 and 120° C. In some aspects, the phase change inks can be solid at room temperature and fluid at temperatures above the phase change temperature. In some aspects, the phase change inks can have a viscosity at jetting temperature between, for example, but not limited to, 0.5 to 50 cps, or more particularly 5 to 20 cps.

In some aspects, a product, for example, but not limited to, a tablet can be formed by the process. The DDD, or for example a tablet, can have a variety of properties, for example, but not limited to a linear drug release profile, a pulsed drug release profile, a targeted release profile to specifically target one or more diseased sites, a fast disintegrating tablet (FDT) profile, a controlled release of a single or multi-drug profile, a DDD having a liquid portion and other personalized drug profiles, such that the DDD is tailored for a specific release rate for a particular treatment and/or a particular patient.

In some aspects the method can include controlling the ejecting by computer-aided design controller. The controller can be implemented in a variety of ways, for example, but not limited to hardware, software, or combinations of hardware and software.

In some aspects, the DDD can be formed by printing a scaffold-type structure with the 3DP system and the computer-aided design controller. The scaffold-type structure can enable a variety of DDD to be formed having different drug release properties that provide a more personalized patient care treatment.

In some aspects, the method can include drying the one or more layers of the DDD. The drying can include applying heat from one or more temperature controlled devices. The temperature controlled device can include, for example, but not limited to, an oven, an apparatus arranged to produce radiation at infrared or microwave frequencies. The drying or heating of the DDD during the formation process of the one or more layers can provide a more consistent DDD.

In some aspects, the one or more excipients can include, but are not limited to, animal waxes such as beeswax, lanolin, spermaceti wax, shellac wax, mink wax, stearic acid, plant waxes, such as apple peel wax, orange peel wax, avocado wax, carnauba wax, Japan wax, castor wax, candelila wax, bayberry wax, esparto wax, jojoba wax, ouricury wax, rice bran wax, soy wax, cetyl esters, palm kernel wax, spent grain wax, sunflower wax, mineral waxes such as ceresin, montan wax, ozokerite, peat wax, petroleum waxes such as microcyrstalline wax, paraffin, petroleum jelly, synthetic waxes such as, polyethylene wax, PEG wax, Fischer-Tropsch wax, hydrogenated oils, sugar alcohols such as sorbitol, maltitol, xylitol, other low melting point substances such as zinc stearate, tagatose, sucrose, raffinose, povidone, triglycerides, and their derivatives.

In some aspects, the forming can include controlling a spatial distribution of the one or more DDD components by arranging a predetermined amount of the one or more DDD components at a predetermined location within the DDD. The spatial distribution can be controlled to produce a DDD with a spatial distribution of API that has a constant drug release rate.

In some aspects, the DDD with the one or more layers are formed as a multilayer shell. A buffer region can be formed between the multilayer shells to produce a DDD having a predetermined delay release time for the API. An outer shell can be formed on the DDD that is arranged to provide a protective coating. The protective coating can include a polymer and various other components, wherein the various other components can include, for example, but not limited to, a pH-dependent solubility, a slow or pH-dependent rate of swelling, dissolution or erosion. The protective coating can include a polymer with a bio-adhesive property. The protective coating can include a coating that is degradable by, for example, but not limited to, a microbial enzyme in a human's colon.

In accordance with aspects of the present disclosure a system is described that includes a three-dimensional printing apparatus including: a plurality of reservoirs arranged to house one or more active pharmaceutical ingredients and one or more excipients, wherein the one or more active pharmaceutical ingredients and the one or more excipients are phase change inks; a plurality of nozzles arranged in communication with the plurality of reservoirs and arranged to jet the one or more active pharmaceutical ingredients and the one or more excipients on to a substrate, the substrate arranged to receive the jetted on or more active pharmaceutical ingredients and the one or more excipients; and a controller configured to control the operation of the plurality of reservoirs and the plurality of nozzles to produce a drug delivery device.

In accordance with aspects of the present disclosure, a drug delivery device is described and can include a solid matrix comprising one or more phase change inks; and one or more active pharmaceutical ingredients dispersed throughout the solid matrix.

In accordance with aspects of the present disclosure, a drug delivery device is described that includes a solid matrix comprising one or more phase change inks; and one or more active pharmaceutical ingredients dispersed throughout the solid matrix.

Additional embodiments and advantages of the disclosure will be set forth in part in the description which follows, and can be learned by practice of the disclosure. The embodiments and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate several embodiments of the disclosure and, together with the description, serve to explain the principles of the disclosure.

DESCRIPTION OF THE EMBODIMENTS

Reference will now be made in detail to various exemplary embodiments of the present application, examples of which are illustrated in the accompanying drawings. Wherever possible, the same reference numbers will be used throughout the drawings to refer to the same or like parts.

In accordance with aspects of the present disclosure, inkjet technology is used to directly print various drug delivery devices (DDD) including personalized tablet in three dimensions without powder bed. Phase change inks and aqueous/solvent inks that are pharmaceutically compatible are used as the basic building materials for DDD. The active pharmaceutical ingredients (API) and excipients are dissolved or dispersed in these inks. By controlling the position and volume of placed drops of single or multiple inks, the local microstructure and composition in DDD are tailored to achieve specific drug release profile and desired physical properties. Similarly drug amount, release rate and even multidrugs in a single DDD can be tuned to meet different personal requirement.

Figure 1:
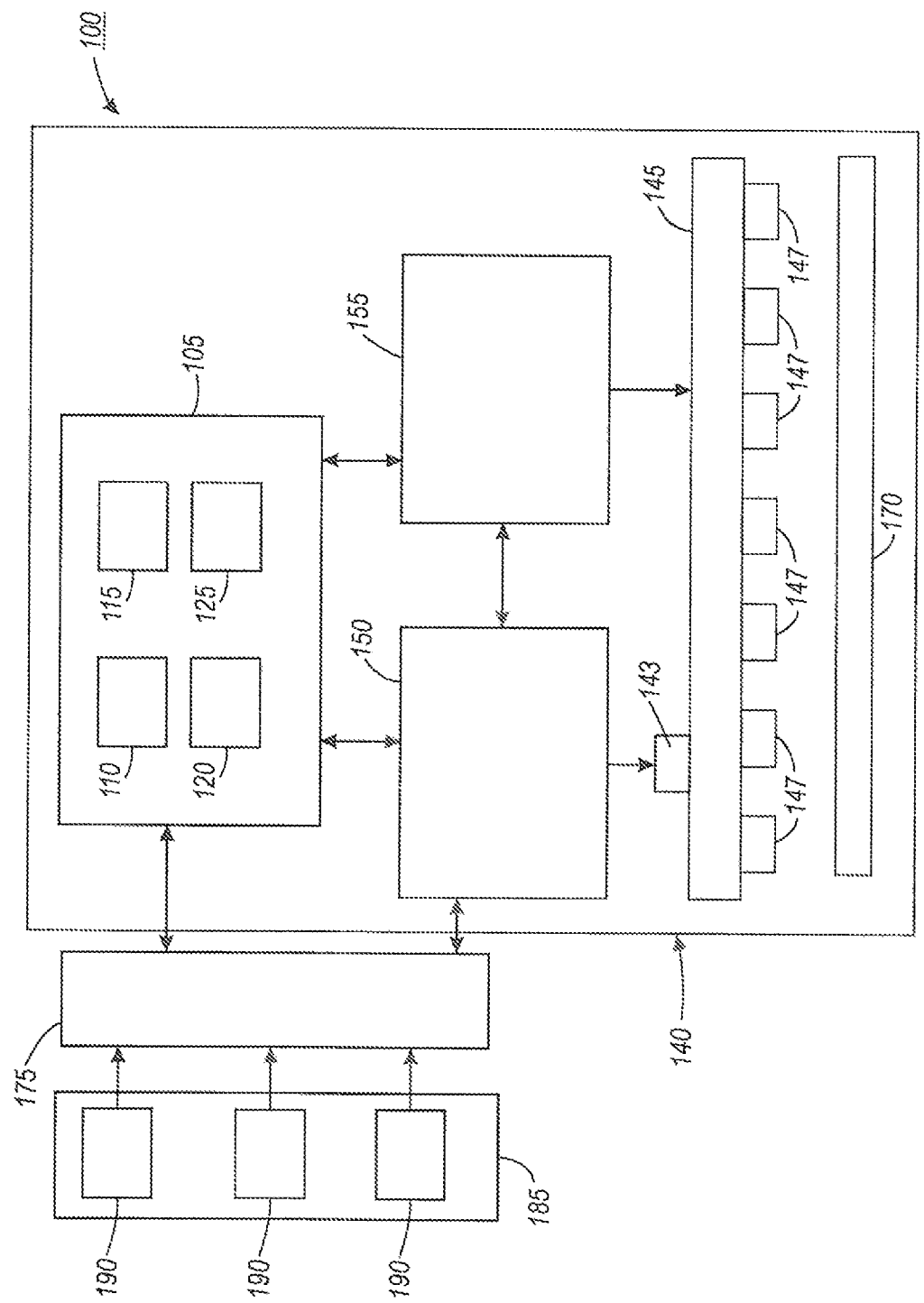
FIG. 1 shows an example three dimensional printing system in accordance with aspects of the present disclosure.

FIG. 1 is a block diagram of a 3D printer system 100 according to an exemplary embodiment of the present disclosure. 3D printer system 100 may include, for example, controller 105, printing apparatus 140, and one or more three dimensional modeling material supply sources such as reservoir apparatuses 185 or reservoir arrays 190.

Controller 105 may include, for example, processor 110, memory unit 115, software code 120, and communications unit 125. Other configurations may be used for a controller or control unit. Control functionality may be spread across units, and not all control functionality may be within system 100. For example, a separate unit, such as a personal computer or workstation, or a processing unit within a supply source such as a reservoir may provide some control or data storage capability. Communications unit 125 may, for example, enable transfer of data and instructions between controller 105 and printing apparatus 140, and/or between controller 105 and one or more reservoir apparatuses 185 or reservoir arrays 190.

Printing apparatus 140 may include for example print head 145 can include one or more individual print heads that eject drops of materials to build drug delivery device, a material delivery controller 150 that delivers materials from reservoir to print head, printing tray 170, motion controller 155 that controls the motion and position of both print head and printing tray, a set of valves (wherein set may include one item) such as a valve matrix 175, leveler (not shown) that levels the surface of each layer of drug delivery device, curer (not shown) that cures or fixes the each layer of drug delivery device and any other suitable components. Print head 145 may further include a small ink storage unit 143 severed as a buffer for jetting materials. Printing apparatus 140 may include other suitable combinations of components.

Material supply sources, such as reservoir apparatus 185, may be situated within printing apparatus 140 or external to printing apparatus 140, and may be situated in a separate unit connected to printing apparatus 140. One or more reservoir arrays 190 may be situated in one or more independent units, connectable to printing apparatus 140. One or more reservoir apparatuses 185 and/or reservoir arrays 190 may be connected to valve 175 or other set of valves via, for example, tubes carrying building material. Reservoir apparatuses 185 and/or reservoir arrays 190 may include one or more sensors (not shown) for each reservoir, to determine the status of the modeling material in one or more reservoirs. Reservoir apparatus 185 may provide, for example, model material and/or support material for use by printing apparatus 140, to print 3D objects. Reservoirs can be any suitable material supply units, for example, cartridges, storage tanks, internal refillable tanks, bags or other units without external casings, etc. One or more sensors (not shown) may be part of reservoir apparatus 185.

The one or more reservoir arrays can include pharmaceutically compatible phase change inks that can include API and excipients (pharmaceutically inactive ingredient), such as binders, diluents, retardants, disintegrants, and lubricants. In some aspects of the present disclosure, the phase change inks can be solid at room temperature and can become jettable liquid at higher temperatures to form the scaffold of DDD or even the whole DDD. As used herein, the phrase "phase change inks" will mean an ink that is retained in a liquid state for ejection, but solidifies upon application to the DDD. The phase change inks can have a phase change temperature that is a phase change between liquid to solid between 40 and 200° C. In some aspects, the phase change temperature can be between 60 and 120° C. The DDD formed by the phase change inks can have mechanical properties at 25° C. that include friability value, for example, but not limited to, less than 1% of weight, crushing strength, for example, but limited to, from 3 kg to 20 kg, tensile strength, for example, but not limited to, from 0.3 MPa to 5 MPa, brittle fracture index, for example, but not limited to, from 0.1 to 0.7. The jetting viscosity can be between 0.5 and 50 cps. Additional pharmaceutically compatible phase change ink or aqueous/solvent inks can be stored in reservoir apparatus 185 and/or reservoir arrays 190 to be jetted by print head 145 to help the control of inner structure and composition of DDD.

In some aspects, if aqueous/solvent inks are used, quick drying process may be needed after one or layers are printed. The API and excipients are dissolved or dispersed in these inks. For instance, aqueous/solvent inks can contain soluble API or excipients, wax based phase change inks can contain lipophilic API and excipients, insoluble drug particles can be dispersed in one of these inks. Color agents, dyes or pigments, can be added to these inks as well. Excipients may also be completely replaced by the phase change ink. Excipients are used under circumstances that call for improved mechanical strength or structure, or special DDD purposes. Ink components with properties needed to fabricate the DDDs would be apparent to those of ordinary skill in the art including those have been already approved by the FDA.

The spatial distribution of drug concentration in DDD can be achieved by accurately placing the specific amount of the API containing drops at specific locations. The drug release profile and DDD mechanical properties, such as hardness, fiability, porosity can be controlled by patterning drops of one or more inks in three dimensions to form the desired structure, geometry and composition in DDD. The color appearance, resistance to moisture, oxidation and light, as well as surface finish of DDD can be achieved by printing special coating inks on the most outer layers. Otherwise, conventional coating process can be used later to coat the DDD. Drug names, dosages, bar or QR codes can also be printed onto the outside of tablets for identification purposes.

Controller 105 may utilize Computer Object Data (COD) representing an object or a model, such as CAD data in Stereo Lithography (STL) format. Other data types or formats may be used. Controller 105 may convert such data to instructions for the various units within 3D printer system 100 to print a 3D object. Controller 105 may be located inside printing apparatus 140 or outside of printing apparatus 100. Controller 105 may be located outside of printing system 100 and may communicate with printing system 100, for example, over a wire and/or using wireless communications. In some embodiments, controller 105 may include a CAD system. In alternate embodiments, controller 105 may be partially external to 3D printer system 100. For example, an external control or processing unit (e.g., a personal computer, workstation, computing platform, or other processing device) may provide some or all of the printing system control capability.

In some embodiments, a printing file or other collection of print data may be prepared and/or provided and/or programmed, for example, by a computing platform connected to 3D printer system 100. The printing file may be used to determine, for example, the order and configuration of deposition of building material via, for example, movement of and activation and/or deactivation of one or more nozzles 147 of print head 145, according to the 3D object to be built.

Controller 105 may be implemented using any suitable combination of hardware and/or software. In some embodiments, controller 105 may include, for example, a processor 110, a memory 115, and software or operating instructions 120. Processor 110 may include conventional devices, such as a Central Processing Unit (CPU), a microprocessor, a "computer on a chip", a micro controller, etc. Memory 115 may include conventional devices such as Random Access Memory (RAM), Read-Only Memory (ROM), or other storage devices, and may include mass storage, such as a CD-ROM or a hard disk. Controller 105 may be included within, or may include, a computing device such as a personal computer, a desktop computer, a mobile computer, a laptop computer, a server computer, or workstation (and thus part or all of the functionality of controller 105 may be external to 3D printer system 100). Controller 105 may be of other configurations, and may include other suitable components.

Controller 105 may receive data from one or more material supply sources, and control the supply of building material to printing apparatus 140, for example, by controlling the extraction or flow of materials from the printing material sources, such as printing reservoirs. For example, controller 105 may use software code 120 to process data related to the status of building material in one or more supply sources to compute material parameters for building material(s), material required to construct one or more objects, and supply parameters for materials in one or more reservoirs. For example, material status data may indicate types, volumes, masses, or other measures, quality, status etc. of building material in one or more supply sources. For example, material parameters may indicate potential yields during printing usage etc. For example, computations of material required may indicate how much material from one or more material supply sources may be used in constructing one or more objects. For example, supply parameters may indicate or help determine, by controller 105 and/or one or more operators, whether or not to use building material from at least one selected reservoir or other source (e.g., to prevent the need for a source switch during an object build), when to extract building material from one or more reservoirs, and how much building material to extract from one or more reservoirs at any given time, according to the requirements of printing apparatus 140 for a particular object being printed. Controller 105 may be suitably coupled and/or connected to various components of printing apparatus 140, to one or more reservoir apparatuses 185, and to one or more reservoir arrays 190. For example, controller 105 may control valves, pumps, switches, compression or inflation devices, motion units, delivery units, leveling devices, curing devices, or any other system components.

In some aspects of the present disclosure, a post-treatment can be used for DDD. The ink drops may not be well fused together in DDD because drops would not be in the same condition when one molten drop impacts other solidified or partially solidified drops. Slightly melting the drop-drop contacts will increase cohesion force, consequently, the mechanical strength of DDD. In some aspects, a temperature controlled apparatus, for example, an oven can be used to heat the DDD to fuse drops without destroying the inner structure of DDD. An alternative is to use pulsed microwaves to heat the DDD internally. If aqueous/solvent inks are used, the drying of DDD can be performed by applying hot air heat, microwaves and infrared in vacuum conditions or in circulating air/gas flow conditions.

Different types and/or profiles of DDD can be made using the system of FIG. 1. By way of a first example, a linear drug release DDD can be manufactured. In this example, two types of phase change inks, one of which contains API, can be alternately jetted to construct DDD with a desire API spatial distribution that leads to constant drug release rate (linear drug release profile) as DDD is eroded away. The drug release rate at given time is proportional to the product of the total surface area of DDD and drug concentration on the surface layer. As DDD is eroded away in the digestive tract, drug concentration must be increased to compensate for less surface area for constant drug release rate. The required API spatial concentration depends on DDD shape and how DDD is eroded.

Figure 2:
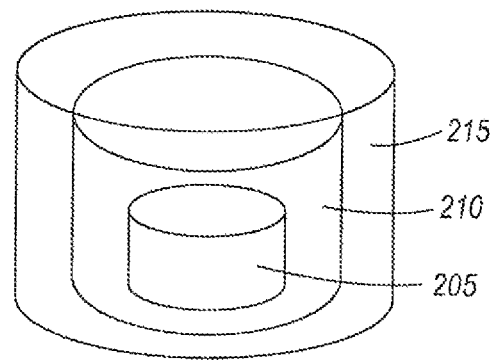
FIG. 2 shows an example drug delivery device in accordance with aspects of the present disclosure.

By way of a second example, a pulsed DDD can be manufactured. The pulsed drug release profile, as shown in FIG. 2, can be achieved by multilayered, core-shell structure DDD using our fabrication method. In the core-shell structure DDD, buffer region 210 can be formed between core 205 and shell 215 to produce a desired delay release time. Similarly, the multipulsed release DDD can also easily be prepared by establishing isolated drug-rich layers or regions in DDD.

Figure 3:
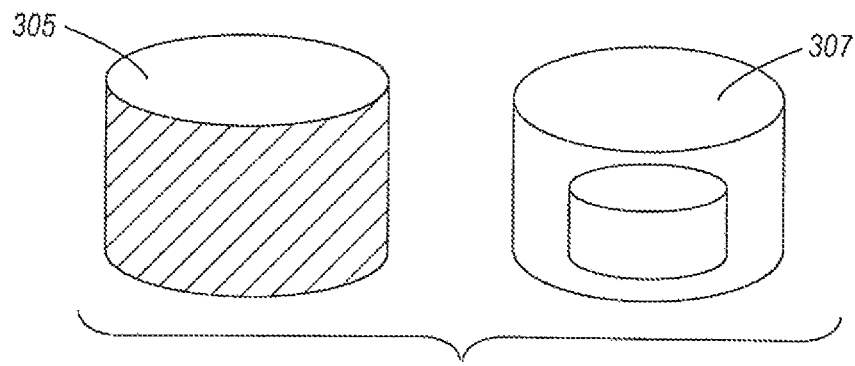
FIG. 3 shows another drug delivery device in accordance with aspects of the present disclosure.

By way of a third example, a targeted DDD can be manufactured, as shown in FIG. 3. Advantage of targeting drugs specifically to the diseased site can include reduced incidence of systemic side effects, lower dose of drug, supply of the drug to the biophase only when it is required and maintenance of the drug in its intact form as close as possible to the target site. For instance, colon targeted DDD can be implemented by jetting special inks on DDD surface to form protective coating 305 or protective out layers 307. These coating inks may include polymers with a pH-dependent solubility, slow or pH-dependent rate of swelling, dissolution, or erosion, degradable by the microbial enzymes in the colon, and polymers with bio-adhesive properties.

By way of a fourth example, a Fast Disintegrating Table can be manufactured. Fast disintegrating tablets (FDT) are tablets that dissolve or disintegrate in the mouth in the absence of additional water for easy administration of API. The advantages of FDT include administration to patients who have difficulty swallowing, more rapid drug absorption, patient convenience and improved patient compliance. Inks with excipients that have high wettability and swelling ratio can be used as major materials for building FDT in addition to phase change inks. The internal structure and composition of FDT are optimized to gain maximum porosity and maintain acceptable mechanical strength. The formed tablets may require post-treatment to remove excessive water/solvent and improve mechanical strength without affecting the porosity and wettability. The final tablets will have the properties of fast absorption or wetting into the tablets and disintegration of tablets into small pieces for fast dissolution. In some aspects, A FDT tablet can be manufactured by creating a strong shell with several hollow spaces in which loose API containing particles or fluid are formed by drops.

Figure 4:
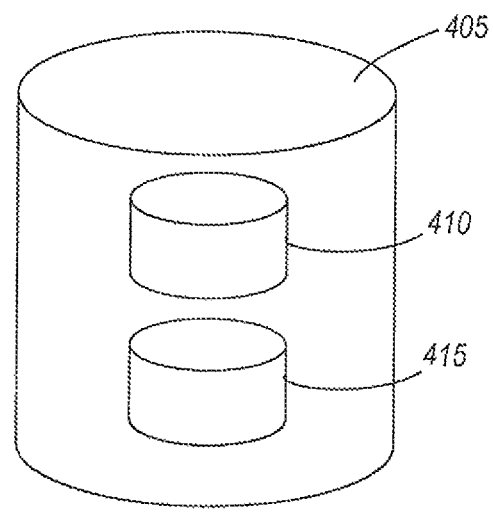
FIG. 4 shows another drug delivery device in accordance with aspects of the present disclosure.

By way of a fifth example, a controlled release of multi-drugs in a single DDD can be manufactured as shown in FIG. 4. Combination dosage forms tend to be more convenient for medical patients than signal dosage forms. Often the treatment of various disorders with multiple drug therapy may require different release rates for each drug. A single dosage form 405 can be manufactured that combines multiple drugs 410, 415 that can have separate domains for drug release at the different models or rates. In some aspects, extra printheads 145 can be added to eject inks containing different drugs in reservoir apparatus 185 and/or reservoir arrays 190. In some aspects, the release profile of each drug can be achieved in the same way of single drug DDD as described above.

By way of a sixth example, a liquid containing DDD can be manufactured. One or more API containing liquid materials can be sealed inside small closed pockets inside solid dosage, which can give greater flexibility for API selection and improves drug absorption, for example, aqueous soluble API, and/or solvent soluble API, and/or lipophilic API, and/or insoluble API in a single DDD.

By way of a seventh example, a personalized DDD can be manufactured. Drug content, release rate and even multidrugs in a single DDD can be tuned to meet different personal requirements. In some aspects, a methodology for personalization in medication, in particular, providing true designer's drugs, a new method for rapid prototyping and drug trials, and creating a unique market can be created. The benefits to patients and pharmacists are a better managed medication system and providing individual systems solutions. For doctors, treating patients as an integrated "whole" with patient specific quantity and combination of medications. The overall impact to the society can be better medical responses, easier doctor-patient relationship, and an overall better patient care. Personalizing medications can thus make "designer's" drugs into a truly reality.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "an acid" includes two or more different acids. As used herein, the term "include" and its grammatical variants are intended to be non-limiting, such that recitation of items in a list is not to the exclusion of other like items that can be substituted or added to the listed items.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A method of forming a layer of at least a portion of a drug delivery device (DDD) comprising:
    providing a substrate;
    providing a first pharmaceutically compatible phase change ink comprising (a) a color agent, a dye, or a pigment and (b) one or more DDD components dissolved or dispersed therein, wherein the first pharmaceutically compatible phase change ink is a solid at room temperature and has a phase change temperature between 40 and 200° C. and wherein the one or more DDD components include one or more excipients selected from the group consisting of sugar alcohols, zinc stearate, tagatose, sucrose, raffinose, povidone, and triglycerides;
    heating the pharmaceutically compatible phase change ink above its phase change temperature to form a first fluid ink;
    ejecting, by one or more nozzles, the first fluid ink onto at least a portion of the surface of the substrate, where it solidifies to form a first layer on the substrate,
    providing an aqueous or solvent ink, the aqueous or solvent ink comprising one or more DDD components; and
    ejecting, by one or more nozzles, a portion of the aqueous or solvent ink onto at least a portion of the surface of the substrate and/or onto the first layer; and drying the ejected aqueous or solvent ink to form a second layer.

2. The method of claim 1, wherein the one or more DDD components includes one or more active pharmaceutical ingredients (API).

3. The method of claim 1, wherein the DDD is a tablet.

4. The method of claim 1, further comprising controlling the ejecting by computer-aided design controller.

5. The method of claim 1, wherein the first pharmaceutically compatible phase change ink has a jetting viscosity between 0.5 to 50 cps.

6. The method of claim 1, wherein the drying includes applying heat from a temperature controlled device, wherein the temperature controlled device is selected from the group consisting of: an oven, an apparatus arranged to produce radiation at infrared frequencies, and an apparatus arranged to produce radiation at microwave frequencies.

7. The method of claim 1, wherein the ejecting includes controlling spatial distribution of the one or more DDD components by arranging a predetermined amount of the one or more DDD components at a predetermined location within the DDD.

8. The method of claim 7, wherein the DDD components comprise an active pharmaceutical ingredient (API) and the spatial distribution is controlled to produce a DDD with a spatial distribution of API that has a constant drug release rate.

9. The method of claim 1, wherein the DDD comprises a multilayer shell, the first layer and at least one additional layer form the multilayer shell, and the first layer or the additional layer comprises an active pharmaceutical ingredient (API).

10. The method of claim 9, further comprising forming a buffer region between the first layer and the additional layer to produce a DDD having a predetermined delay release time for the API.

11. The method of claim 9, wherein the DDD comprises a protective coating on the outer surface thereof.

12. The method of claim 1, wherein the DDD is a fast disintegrating tablet.

13. The method of claim 2, wherein the one or more API are selected to treat one or more diseases.

14. The method of claim 1, further comprising forming a liquid active pharmaceutical ingredient (API) section within the DDD.

15. The method of claim 1, wherein the one or more nozzles are part of a three-dimensional printing (3DP) system.

16. The method of claim 1, wherein the DDD comprises a second pharmaceutically compatible phase change ink comprising one or more DDD components.

* * * * *